United States Patent
Lee et al.

(10) Patent No.: US 10,289,953 B2
(45) Date of Patent: May 14, 2019

(54) DOSE OPTIMIZATION BASED ON OUTCOME QUALITY

(71) Applicant: KONINKLIJKE PHILIPS N.V., Eindhoven (NL)

(72) Inventors: Michael Chun-chieh Lee, Lexington, MA (US); Eric Cohen-Solal, Ossining, NY (US)

(73) Assignee: Koninklijke Philips N.V., Eindhoven (NL)

( * ) Notice: Subject to any disclaimer, the term of this patent is extended or adjusted under 35 U.S.C. 154(b) by 662 days.

(21) Appl. No.: 14/365,267

(22) PCT Filed: Dec. 7, 2012

(86) PCT No.: PCT/IB2012/057055
§ 371 (c)(1),
(2) Date: Jun. 13, 2014

(87) PCT Pub. No.: WO2013/088318
PCT Pub. Date: Jun. 20, 2013

(65) Prior Publication Data
US 2014/0304206 A1    Oct. 9, 2014

Related U.S. Application Data

(60) Provisional application No. 61/569,876, filed on Dec. 13, 2011.

(51) Int. Cl.
*A61B 6/00* (2006.01)
*G06N 5/04* (2006.01)
(Continued)

(52) U.S. Cl.
CPC .............. *G06N 5/04* (2013.01); *A61B 6/032* (2013.01); *A61B 6/542* (2013.01); *G16H 40/40* (2018.01); *G06F 19/321* (2013.01)

(58) Field of Classification Search
None
See application file for complete search history.

(56) References Cited

U.S. PATENT DOCUMENTS 6,658,396 B1 * 12/2003 Tang .................. G01N 33/5091
600/300
8,483,358 B2    7/2013 Allison
(Continued)

FOREIGN PATENT DOCUMENTS

| EP | 1354554 A2 | 10/2003 |
|----|-----------|---------|
| JP | 2011110289 A | 6/2011 |
| WO | 2008103834 A1 | 8/2008 |

OTHER PUBLICATIONS

Zhang, J. et al., "The Optimization of CT Parameters Setting of Children with Head Injury", Radiol Practice, vol. 20, No. 10, (2005) pp. 893-896.

*Primary Examiner* — Paulinho E Smith

(57) ABSTRACT

A system includes a modeler that generates a model which models a quality of findings in radiologist reports as a function of deposited dose of scans from which the radiologist reports are created and a dose optimizer that determines an optimal dose value for a planned scan based on the model and one or more optimization rules. A method includes generating a model which models a quality of findings in radiologist reports as a function of deposited dose of scans from which the radiologist reports are created and determining an optimal dose value tar a planned scan based on the model and one or more optimization rules.

20 Claims, 4 Drawing Sheets

(51) Int. Cl.
*A61B 6/03* (2006.01)
*G16H 40/40* (2018.01)
*G06F 19/00* (2018.01)

(56) References Cited

U.S. PATENT DOCUMENTS

| | | | |
|---|---|---|---|
| 2006/0010090 A1* | 1/2006 | Brockway | A61B 5/0002 706/46 |
| 2007/0094182 A1* | 4/2007 | Jung | G06F 19/3406 706/21 |
| 2008/0103834 A1* | 5/2008 | Reiner | G06F 19/345 705/3 |
| 2009/0157577 A1* | 6/2009 | Chauhan | G03F 7/705 706/16 |
| 2010/0121473 A1* | 5/2010 | Ding | D21G 9/0018 700/104 |
| 2010/0204920 A1* | 8/2010 | Dranitsaris | G06F 19/3431 702/19 |
| 2011/0153547 A1* | 6/2011 | McNutt | G06F 19/3443 706/54 |
| 2011/0225112 A1* | 9/2011 | Cameron | G06F 19/3437 706/20 |
| 2011/0270623 A1 | 11/2011 | Reiner | |
| 2013/0041681 A1* | 2/2013 | Cohen-Solal | G06F 19/3487 705/2 |
| 2013/0151284 A1* | 6/2013 | Cohen-Solal | G06Q 10/063114 705/2 |
| 2013/0311200 A1* | 11/2013 | Cohen-Solal | G06F 19/321 705/2 |
| 2014/0010432 A1* | 1/2014 | Cohen-Solal | G06F 19/321 382/131 |
| 2014/0019396 A1* | 1/2014 | Carlsgaard | G06N 5/02 706/46 |
| 2014/0304206 A1* | 10/2014 | Lee | G06F 19/3412 706/47 |
| 2014/0379378 A1* | 12/2014 | Cohen-Solal | G06F 19/3487 705/3 |
| 2014/0379629 A1* | 12/2014 | Loew-Baselli | G06F 19/70 706/52 |
| 2016/0070871 A1* | 3/2016 | Heinonen | G06F 19/345 706/12 |
| 2016/0162797 A1* | 6/2016 | Thorpe | A61B 5/4839 706/52 |

* cited by examiner

DOSE OPTIMIZATION BASED ON OUTCOME QUALITY

This application is a national stage application under 35 U.S.C. § 371 of International Application No. PCT/IB2012/057055 filed on Dec. 7, 2012 and published in the English language on Jun. 20, 2013 as International Publication No. WO/2013/088318, which claims priority to U.S. Application No. 61/569,876 filed on Dec. 13, 2011, the entire disclosures of which are incorporated herein by reference.

The following generally relates to imaging and more particularly to optimizing ionizing radiation dose of a scan based on the radiation dose utilized with previous scans and the radiologist reports corresponding to those scans.

Imaging modalities such as computed tomography (CT) and x-ray utilize ionization radiation to image a subject. Unfortunately, ionizing radiation may increase a risk of damage to living tissue, radiation sickness, cancer, and death to a human or animal subject. With CT, the radiation dose deposited in the subject depends on factors such as tube current (milliampere-second, or mAs), tube voltage (peak kilovolts, or kVp), pitch/exposure time (for helical scans), slice thickness and spacing (for axial scans), the number of scans in a study, and patient physiology (e.g., thicker or thinner). Deposited dose has been measured using CT dose index (CTDI) in units of milligray (mGy) and dose-length product (DLP) in units of mGy x centimeter (cm).

The technologist planning and performing a scan can reduce the deposited dose to the subject by decreasing mAs, kVp and/or the number of scans, and/or increasing the pitch, slice thickness and/or slice spacing. However, image noise is inversely proportional to radiation dose, and thus arbitrarily reducing radiation dose not only reduces dose but also increases image noise in the acquired data, which is propagated to the image data during reconstruction, reducing visual image quality (e.g., decreased signal to noise or contrast to noise, etc.). Increasing radiation dose, within a reasonable range, generally will improve visual image quality. However, increasing visual image quality does not necessarily increase the diagnostic value of the image data.

The technologist typically sets these parameters, sometimes in conjunction with a radiologist, based on the physical characteristic of the subject, the clinical indications (i.e., the reasons for the scan), etc. In many cases, the parameters are encapsulated as fixed protocols, which direct a certain level of radiation to be applied. However, this level of radiation is defined through the expertise of the technologists and radiologists and their experience in acquiring and reading patient images, and objective measures such as contrast to noise, signal to noise, MTF estimates, etc. may not be reliable for determining an optimal level of dose for a particular subject with respect to diagnostic value.

Aspects described herein addresses the above-referenced problems and others.

In one aspect, a system includes a modeler that generates a model which models a quality of findings in radiologist reports as a function of deposited dose of scans from which the radiologist reports are created and a dose optimizer that determines an optimal dose value for a planned scan based on the model and one or more optimization rules.

In another aspect, a method includes generating a model which models a quality of findings in radiologist reports as a function of deposited dose of scans from which the radiologist reports are created and determining an optimal dose value for a planned scan based on the model, a group assignment for the planned scan, and one or more optimization rules.

In another aspect, a system includes an imaging system, a report and dose evaluator and a validator. The imaging system is configured to scan a patient based on predetermined scan parameters of a planned scan of a patient, wherein the predetermined scan parameters include at least one scan parameter that affects a dose delivered to the patient when the patient is scanned. The report and dose evaluator determines an optimal dose for a scan of the patient based on a relationship between a quality of findings in radiologist reports and measured deposited dose of previously performed scans of patients. The validator compares an estimated dose value of the planned scan and the optimal dose value and generates a signal indicating whether the estimated dose value exceeds the optimal dose value. In response to the estimated dose value not exceeding the optimal dose value, the imaging system performs the scan based on the predetermined scan parameters.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with a report and dose evaluator, a validator and a data repository.

FIG. 2 schematically illustrates an example of the report and dose evaluator of FIG. 1.

FIG. 3 graphically illustrates a positive findings curve as a function of scan dose.

The following generally describes an approach for determining a relationship between a quality of (e.g., positive findings from) a radiologist report and a measured dose deposited to a patient during of the corresponding scan and/or utilizing the relationship to validate a planned scan to be performed based on an estimated dose of the planned scan.

Figure 1:
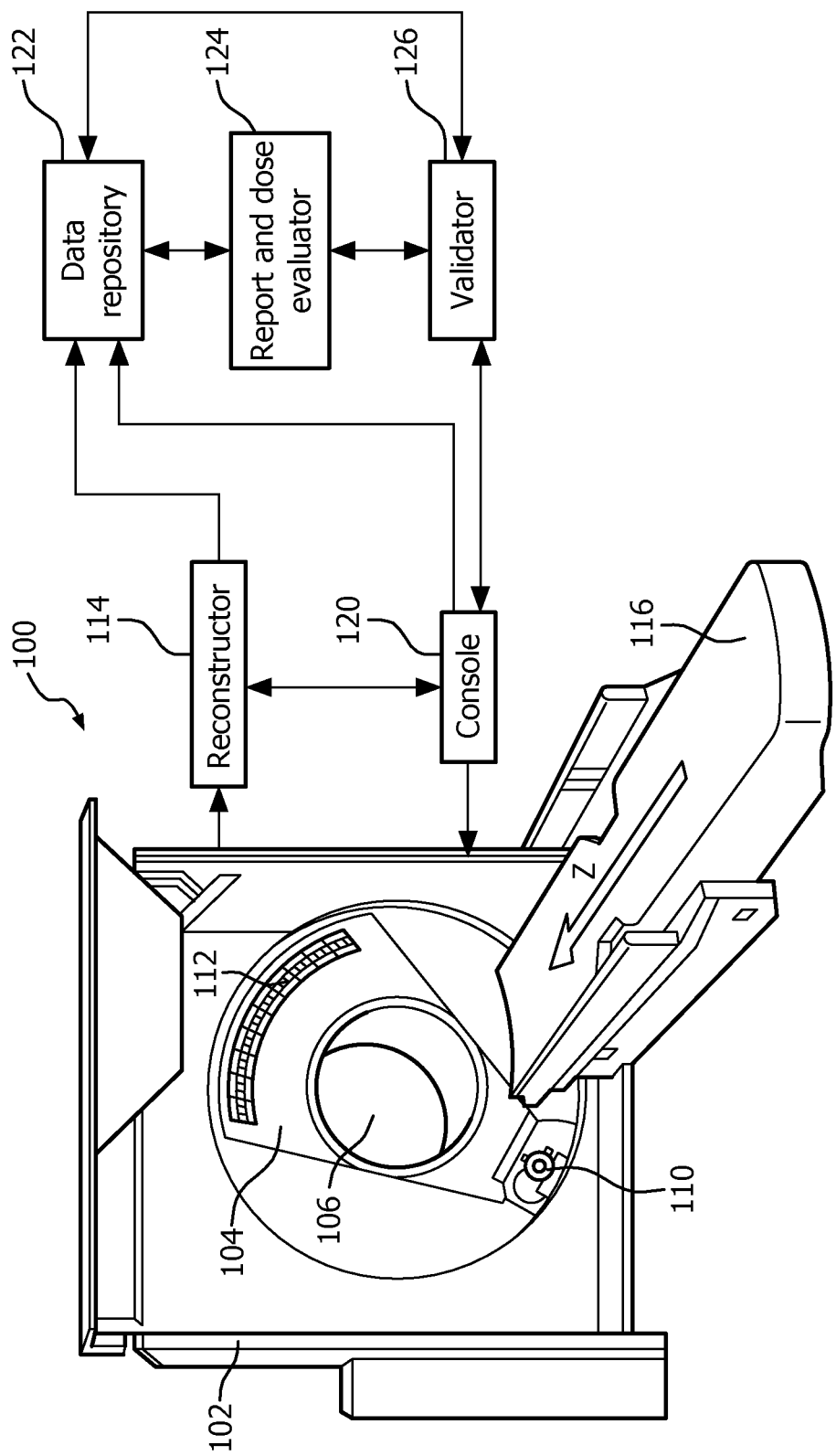

Initially referring to FIG. 1, an imaging system 100 such as a computed tomography (CT) scanner is schematically illustrated. It is to be understood that the imaging system 100 can be any imaging system which utilizes ionizing radiation to scan subjects. The illustrated imaging system 100 includes a stationary gantry 102 and a rotating gantry 104. The rotating gantry 104 is rotatably supported by the stationary gantry 102 and rotates around an examination region 106 about a z-axis.

A radiation source 110, such as an x-ray tube, is rotatably supported by the rotating gantry 104. The radiation source 110 rotates with the rotating gantry 104 and emits ionizing radiation that traverses the examination region 106. A one or two dimensional radiation sensitive detector array 112 subtends an angular arc opposite the radiation source 110 across the examination region 106. The detector array 112 detects ionizing radiation traversing the examination region 106 and generates projection data indicative thereof.

A reconstructor 114 reconstructs the projection data and generates volumetric image data indicative thereof. The reconstructor 114 may employ a conventional filtered-back-projection algorithm, a cone beam algorithm, an iterative algorithm and/or other algorithm. A subject support 116, such as a couch, supports the subject in the examination region 106.

A general-purpose computing system or computer serves as an operator console 120. The console 120 includes a human readable output device such as a monitor or display and an input device such as a keyboard, mouse, etc. Software resident on the console 120 allows the operator to interact with the scanner 100 via a graphical user interface (GUI) or otherwise. This interaction may include selecting an imaging protocol and/or setting imaging parameters such kVp, mAs, temporal resolution, angular sampling, etc.

A data repository 122 includes one or more of a picture archiving and communication system (PACS), a radiology information system (RIS), a hospital information system (HIS), an electronic medical record (EMR), and/or other data storage device. Image data generated by the imaging system 100 and/or other imaging system can be stored in the data repository 122. Information related to the scan that can be stored in the data repository 122 includes the imaging protocol, dose related imaging parameters (kVp, mAs, etc.), dose measurements (CTDI and/or DLP), clinical indications, an identification of the interpreting radiologist, the radiologist report, patient demographics, the scanned anatomy, etc. The data repository 122 can be local, remote and/or part local and part remote from the system 100.

A report and dose evaluator 124 evaluates content of the radiologist report and measured dose for one or more scans in the data repository 122 and/or other data repository. As described in greater detail below, the report and dose evaluator 124 determines, based on the evaluation, a relationship between a quality of the report and the measured dose and generates a signal or data indicative thereof. Generally, simply increasing dose, within a reasonable range, will improve image quality. However, simply increasing dose does not necessarily improve the rate of positive findings by the radiologists. The generated data allows for optimizing dose for a patient to be scanned based on the rate of positive findings in addition to or in alternative to optimizing dose for visual quality of the image.

A validator 126 can be used to validate, based on the data generated by the report and dose evaluator 124, imaging settings of planned scan selected and/or entered by an imaging technologist for a patient to be scanned. Such validation may include estimating and/or obtaining an estimated dose for the planned scan and comparing the estimated dose with an optimal dose for the scan as determined by the report and dose evaluator 124. In one instance, the estimated dose for the planned scan for the patient is obtained based on information of the patient extracted from the data repository 122 and the same criteria from the grouping criteria 208 that was used to group patients. For example, this information is used to map the patient to the correct group, and then the optimal dose value for this group can be located and obtained. The validator 126 can send a signal to the console 120 indicating whether the estimated dose satisfies the optimal dose value.

Where the accumulated dose of the patient is also known, the signal may also indicate whether the scan will increase the patient's dose beyond a predetermined recommended accumulated dose level. The radiologist can determine whether to continue with the current dose level or change scan parameters to reduce the dose level based on the accumulated dose. Moreover, the validator may be able to offer suggestions for parameter value change to facilitate further reducing dose in light of accumulated dose. In one instance, this may include finding a study for another patient where the optimal dose value would cause the accumulated dose to exceed a predetermined recommended accumulated dose level and suggests similar scan parameters.

It is to be appreciated that the report and dose evaluator 124 and/or the validator 126 can be implemented via one or more processors executing one or more computer readable instructions encoded or embedded on computer readable storage medium such as physical memory. Such a processor(s) can be part of the console 120 and/or other computing device such as a dedicated visualization computer, and/or other computing device. Additionally or alternatively, the processor can execute at least one computer readable instructions carried by a carrier wave, a signal, or other non-computer readable storage medium such as a transitory medium.

Figure 2:
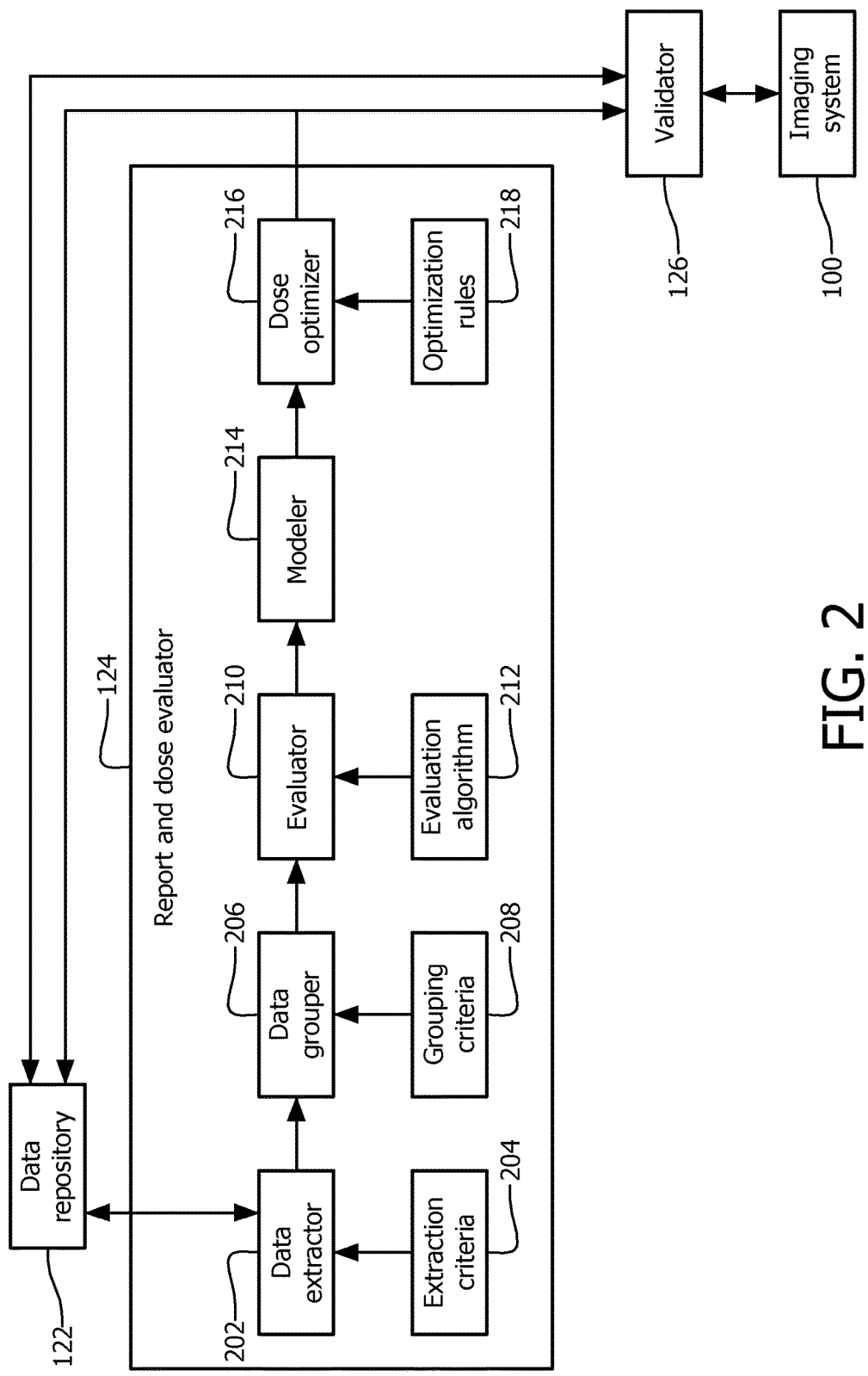

FIG. 2 schematically illustrates an example of the report and dose evaluator 124 in connection with the imaging system 100, the data repository 122 and the validator 126.

A data extractor 202 extracts data from the data repository 122 for evaluation. In the illustrated embodiment, the data extractor 202 extracts data from the data repository 122 based on extraction criteria 204. By way of non-limiting example, in one instance the extraction criteria 204 may cause the data extractor 202 to extract patient studies including the radiologist reports, ionizing radiation dose measurements and/or parameters used to determined dose, imaging protocols, the identity of the anatomy scanned, clinical indications, etc. of the studies. The extraction criteria 204 can be predetermined and/or user defined.

A data grouper 206 groups the extracted data into one or more groups. In the illustrated embodiment, the data grouper 206 groups the extracted data based on grouping criteria 208. By way of non-limiting example, in one instance the grouping criteria 208 causes the data grouper 206 to group the extracted studies based on imaging protocol, anatomy scanned, clinical indication, demographics, and/or interpreting radiologist. Where the interpreting radiologist is used, the data can be grouped based on the radiologist. The grouping can be performed at a single level or multiple levels where grouped data is grouped into sub-groups. The grouping criteria 208 can be predetermined and/or user defined.

An evaluator 210 evaluates the data in each group. In the illustrated embodiment, the evaluator 210 at least evaluates the radiologist report and the measured dose of each study based on one or more evaluation algorithms 212. The evaluation may include the entire report or one or more particular sub-sections of the report, such as the "Findings", "Conclusions", and/or other section. Where the interpreting radiologist is taken into account, the evaluation can be normalized across radiologists. Thus, the different reporting styles of each radiologist (one radiologist at a dose level x may have an inherently more "uncertain" style of reporting than another radiologist at the same dose level) can be considered.

In one instance the one or more evaluation algorithms 212 causes the evaluator 210 to determine a presence, an absence, and/or a frequency of one or more of the following metrics on each of the reports in each of the groups: direct counts of terms of uncertainty (e.g., "may be consistent with", "possibly", "requires further study," etc.); statistical measures of uncertainty based on, e.g., sentiment analysis; presence of positive findings; presence of negative findings; presence of comparison findings with prior report; presence of recommended actions; strength of the recommendation; average number of distinct medical concepts (lower if images of less quality), and/or other metrics.

A modeler 214 models the evaluated data. By way of example, in one non-limiting instance, the modeler 214 employs a mathematical model to model quality of findings in a radiologist report as a function of dose. For example, a nonlinear regression curve may be computed for the data. Note that the individual studies may be placed in bins based on their dose, and the mean or median quality within that dose bin may be computed. Alternatively, every scan can be considered as a separate data point.

It is noted that data extractor 202, data grouper 206, evaluator 210, and modeler 214, can be implemented via one or more processors executing one or more computer readable instructions encoded or embedded on computer readable storage medium such as physical memory to carry out the functions described above. Such a processor(s) can be part of a computing device such as a dedicated visualization computer and/or other computing device. Additionally or alternatively, the processor can execute at least one computer readable instructions carried by a carrier wave, a signal, or other non-computer readable storage medium such as a transitory medium.

Table 1 shows a non-limiting example of dose and positive findings data. Column 1 includes dose data, represented as average CTDI in units of mGy, and column 2 includes the fraction of reports with positive findings. Each row in Table 1 provides values determined from a plurality of individual studies.

TABLE 1

Dose and Positive Findings.

| Average CTDI (mGy) | fraction of reports with positive findings |
|---|---|
| 5 | 0.62 |
| 10 | 0.60 |
| 15 | 0.71 |
| 20 | 0.79 |
| 25 | 0.77 |
| 30 | 0.80 |
| 35 | 0.77 |

Figure 3:
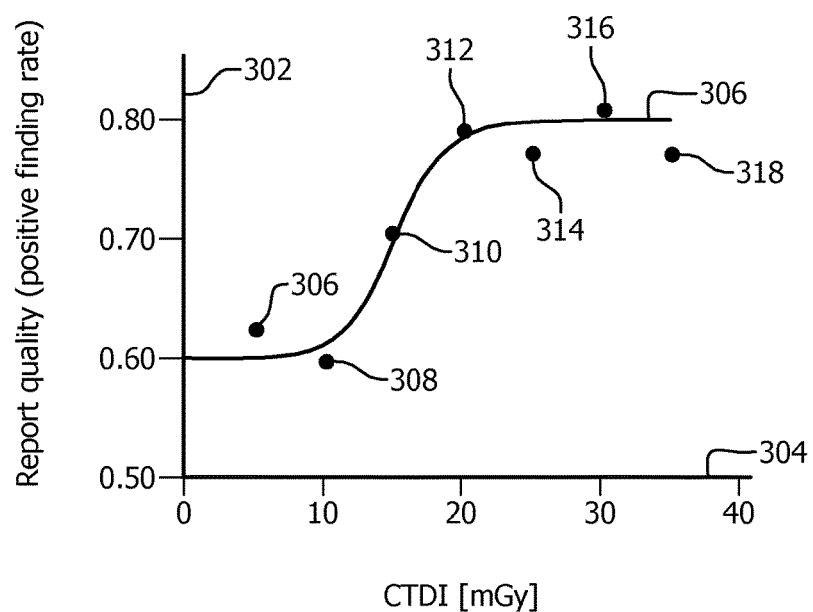

Briefly turning to FIG. 3, the data of Table 1 is graphically depicted. In FIG. 3, a y-axis 302 represents quality of findings and an x-axis 304 represents dose. Using a sigmoid (logistic) function, the modeler 214, in this non-limiting example, fits a curve 306 to data points 308-318 corresponding to the data of Table 1 as follows: $y=A/(1+\exp(-(\text{dose}-B)/C))+D$, where A, B, C, and D are variables such that D represents the minimum value of the fitted regression function, A represents the maximum excursion from D, the variable B represents the dose at which the quality value y is at its half-maximal value, and C defines the steepness of the transition between minimum and maximum values.

A dose optimizer 216 determines an optimal dose value for the group defined by criteria 208 based on the mathematical model, the data used to generate the mathematical model and/or the raw data, and one or more optimization rules 218. By way of non-limiting example, an optimization rule may cause the dose optimizer 216 to find the CTDI dose value on the curve 306 of FIG. 3 that corresponds to 90% of the distance between a minimum and a maximum report quality. In this example, the dose value is approximately 20 mGy. The optimization rules 218 can be predetermined and/or user defined. The optimal dose value and/or the model can be stored in the data repository 122 and/or other storage device, and/or conveyed to another component such as the validation 126 and/or other device. In one instance, the optimal dose value and/or the model are conveyed to a computing system where one or more of the optimal dose value and/or the model are visually displayed via a monitor.

In one non-limiting example, the validator 126 receives a planned image study from the imaging system and validates the estimated dose for the patient based on the generated optimal dose value. As discussed above, the grouping for the patient is first identified based on the grouping criteria 208. Then the optimal dose value for the grouping can be obtained and compared with the estimated dose. By way of further example, optimum dose for ten different groups (e.g. according to type of clinical problem) may have been previously determined. When a new patient arrives, the patient has to first be placed or mapped to one of the ten groupings, and this is achieved based on the grouping criteria 208. Once the correct grouping is identified, the optimal dose value for the grouping can be obtained. In one instance, if the estimated dose is less than or within a preset range of the optimal dose value, then the validator 126 does nothing. Alternatively, validator 126 conveys a validation signal to the imaging system 100, which then apprises the user that the dose related settings of the planned image study satisfies the optimal dose value. In addition, if the estimated dose does not satisfy the optimal dose value, then the validator 126 conveys a warning signal to the imaging system 100, which then apprises the user that the dose related settings of the planned image study do not satisfy the optimal dose value. The technologist can ignore the warning or change one or more imaging parameters. As noted above, where the accumulated dose of the patient is also known, a signal indicating whether the scan will increase the patient's dose beyond a predetermined recommended accumulated dose level may also be conveyed to the imaging system 100.

Figure 4:
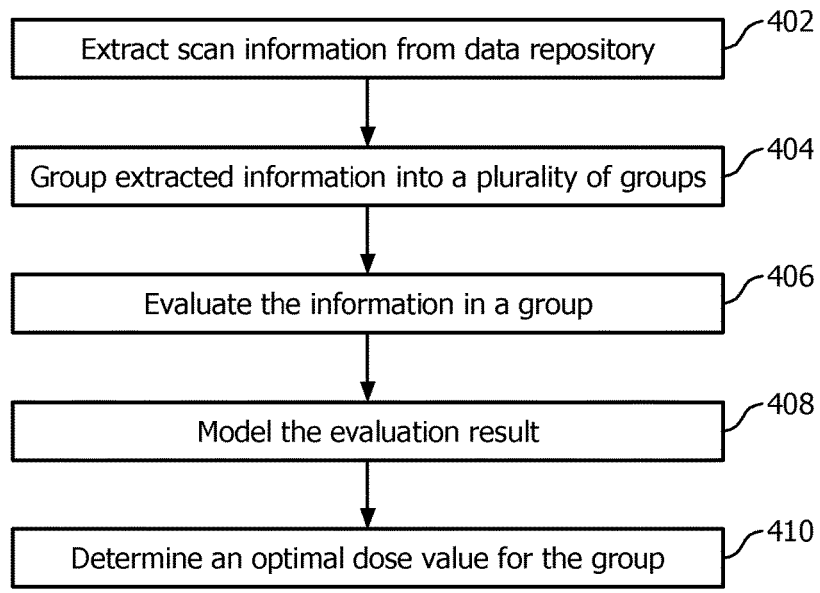
FIG. 4 illustrates an example method for determining a relationship between the information in radiologist reports and the dose level used to generate the imaging data used to create the reports.
Figure 5:
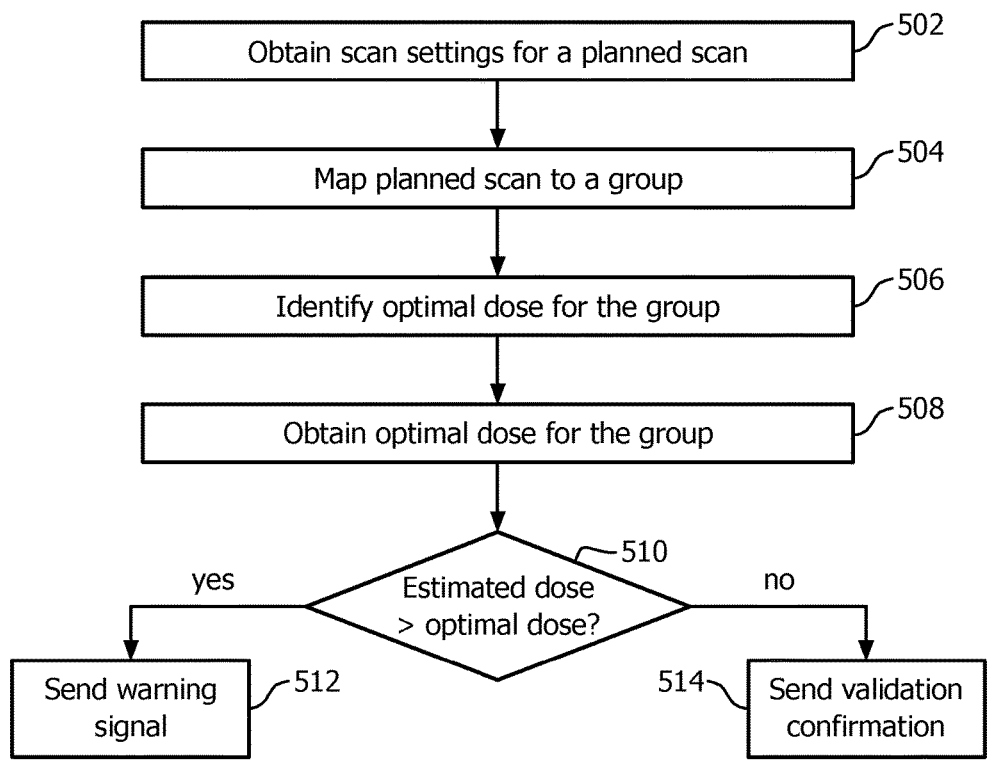
FIG. 5 illustrates an example method for validating dose related imaging setting for a planned scan based on the relationship determined in FIG. 4.

FIGS. 4 and 5 illustrate example methods in accordance with FIGS. 1-3. It is to be appreciated that the ordering of the acts in the methods described herein is not limiting. As such, other orderings are contemplated herein. In addition, one or more acts may be omitted and/or one or more additional acts may be included.

FIG. 4 illustrates an example method for determining a relationship between quality of findings in a radiologist report for imaging data and the dose deposited when acquiring the imaging data.

At 402, scan information, such as a radiologist report, dose measurements and/or parameter used to measure dose, for one or more imaging studies, is extracted from a data repository. Other information which may be extracted includes imaging protocol, an identification of the anatomy scanned, clinical indications, interpreting radiologist, and/or other information.

At 404, the extracted data is grouped into a plurality of different groups based on grouping criteria. For example, the data may be grouped based on interpreting radiologist, imaging protocol, anatomy scanned, and/or other information.

At 406, the data in a group is evaluated to determine one or more report quality metrics about the data in that group. As described herein, this may include determining a percentage of positive findings for each of a plurality of levels of dose.

At 408, at least a subset of the one or more metrics is modeled. As described herein, this may include mathematically modeling quality of findings as a function of dose based on the statistics.

At 410, an optimal dose value is determined based on the model (and/or the data used to generate the model) and one or more optimization rules. The optimal dose value and/or the model can be stored and/or conveyed to another device.

Acts 406-410 can be performed for one or more groups of data.

FIG. 5 illustrates an example method for validating imaging settings based on the relationship determined in FIG. 4.

At 502, scan settings, including dose determining parameters and/or an estimated dose, from a planned scan are obtained for a patient.

At 504, the planned scan is mapped to one of a plurality of different groups of scans. In one instance, the plurality of different groups is generated as described at 404 of FIG. 4 or otherwise.

At 506, the optimal dose value for the one of the plurality of different groups of scans is identified.

At 508, the identified optimal dose value is obtained.

At 510, the estimated deposited dose of the planned scan is compared with the dose optimization value. The estimated dose can be determined based on scan parameters affecting dose such as kVp, mAs, etc. as discussed herein.

If the estimated dose exceeds the optimal dose value, then at 512 a warning signal is conveyed to the imaging system, which notifies (e.g., via visual message on the monitor, audible message and/or other message) the technologist setting up and performing the planned imaging study that the dose level of the planned scan does not satisfy the dose optimization value. The technologist can change the dose related image settings or continue as planned.

Otherwise, at 514, a validation confirmation can be conveyed to the imaging system. If the scan would increase the patient accumulated dose beyond a recommended threshold, a notification indicating this can also be conveyed to the imaging system.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
a data acquisition system;
a console, including:
a memory storing a mathematical model; and
a processor configured to:
extract radiology reports and ionizing radiation dose measurements from stored patient studies;
generate, with the mathematical model, a model which models a quality of findings in the radiology reports as a function of deposited dose of scans from the ionizing radiation dose measurements, wherein the quality of findings corresponds to a positive finding rate; and
determine an optimal radiation dose value based on the model and one or more optimization rules;
estimate a radiation dose value for a planned scan; and
control the data acquisition system to acquire projection data indicative of an examination region based on the planned scan in response to the estimated radiation dose value for the planned scan not exceeding the determined optimal radiation dose value, and
an image reconstruction system configured to reconstruct the projection data to generate volumetric image data of the examination region.

2. The system of claim 1, wherein the processor models the quality of findings graphically in a regression curve.

3. The system of claim 1, wherein the one or more optimization rules defines the optimal dose value as a predetermined percentage between a maximum quality and a minimum quality.

4. The system of claim 2, wherein the processor models the quality of findings as: $y=A/(1+\exp(-(\text{dose}-B)/C)+D$, where y represents the quality, D represents a minimum value of the regression curve, A represents a maximum excursion from D, B represents a radiation dose at which y is at a half-maximal value, and C defines a steepness of a transition between the minimum and maximum values.

5. The system of claim 1, wherein the processor individually evaluates groups of related imaging studies and generates the model for a group of the groups based on a result of an evaluation of that group.

6. The system of claim 5, wherein the evaluation is based on a sub-set of sections of the radiology reports.

7. The system of claim 5, wherein the evaluation of the group is normalized across interpreting radiologist.

8. The system of claim 5, wherein the evaluation is specific to a style of a particular interpreting radiologist.

9. The system of claim 5, wherein the evaluation determines at least one of a presence, an absence, or a frequency of one or more of: a count of terms of uncertainty; a statistical measures of uncertainty based on sentiment analysis; a presence of positive findings; a presence of negative findings; a presence of comparison findings with prior report, a presence of recommended actions; a strength of the recommendation; an average number of distinct medical concepts, or other metric.

10. The system of claim 5, wherein the processor groups imaging related data extracted from a data repository into one or more groups and individually evaluates one or more of the groups.

11. The system of claim 10, wherein the processor groups the imaging related data based on one or more of imaging protocol, anatomy scanned, clinical indication, demographics, or interpreting radiologist.

12. The system of claim 1, wherein processor validates scan settings, of the planned scan, related to dose based on the optimal dose value.

13. The system of claim 12, wherein the processor compares the estimated radiation dose value of the planned scan and the optimal radiation dose value and displays a warning signal in response to the estimated dose value exceeding the optimal dose value.

14. The system of claim 12, wherein at least one of the estimated radiation dose value, the optimal radiation dose value or an accumulated dose value of the patient is visually presented via a monitor.

15. A method, comprising:
extracting, with a processor, radiology reports and ionizing radiation dose measurements from stored patient studies;
generating, with the processor, a model which models a quality of findings in radiologist reports as a function of deposited dose of scans from which the radiologist reports are created using the extracted radiology reports and ionizing radiation dose measurements;
determining, with the processor, an optimal radiation dose value based on the model, a group assignment for the planned scan, and one or more optimization rules, wherein the optimal radiation dose value corresponds to a radiation dose value of a scan at which a likelihood of improving a positive finding rate by increasing the radiation dose delivered is less than a predetermined threshold;

estimating, with the processor, a radiation dose value for a planned scan;

controlling, with the processor, data acquisition of an imaging system to acquire projection data indicative of an examination region based on the planned scan in response to the estimated radiation dose value for the planned scan not exceeding the optimal radiation dose value; and reconstructing, with the processor, the projection data to generate volumetric image data of the examination region.

16. The method of claim 15, further comprising:

extracting imaging related data from a data repository into one or more groups, wherein the imaging related data includes image data and one or more of an imaging protocol, dose related imaging parameters, dose measurements, clinical indications, an identification of an interpreting radiologist, a radiologist report, patient demographics, an identification of the scanned anatomy corresponding to the image data;

grouping the extracted imaging related data into a plurality of groups, wherein the extracted imaging related data is grouped based on one or more of imaging protocol, anatomy scanned, clinical indication, demographics, or interpreting radiologist; and evaluating, individually, one or more of the groups of related imaging studies, wherein the evaluation determines at least one of a presence, an absence, or a frequency of one or more of: a count of terms of uncertainty; a statistical measures of uncertainty based on sentiment analysis; a presence of positive findings; a presence of negative findings; a presence of comparison findings with prior report; a presence of recommended actions; a strength of the recommendation; an average number of distinct medical concepts, or other metric.

17. The method of claim 16, further comprising:

assigning the planned scan to a predetermined group of scans;

identifying and obtaining the optimal dose value for the predetermined group of scans;

comparing an estimated dose value of the planned scan and the obtained optimal dose value; and generating a warning signal in response to the estimated dose value exceeding the optimal dose value.

18. The method of claim 15, wherein generating the model includes computing $y=A/(1+\exp(-(\text{dose}-B)/C)+D$, where y represents the quality, D represents a minimum value of a regression function, A represents a maximum excursion from D, B represents a radiation dose at which y is at a half-maximal value, and C defines a steepness of a transition between the minimum and maximum values.

19. A system, comprising:

an imaging system configured to scan a patient based on predetermined scan parameters of a planned scan of a patient, wherein the predetermined scan parameters include at least one scan parameter that affects a dose delivered to the patient when the patient is scanned;

a console with a processor configured to:

determine a quality of findings in radiologist reports as a mathematical function of deposited dose of scans from which the radiologist reports are created, wherein the quality of findings corresponds to a positive finding rate;

determine an optimal dose value for a scan of the patient based on a relationship between the quality of findings and measured deposited dose of previously performed scans of patients;

generating a signal indicating whether the estimated dose value exceeds the optimal dose value; and in response to the estimated dose value not exceeding the optimal dose value, control the imaging system to perform the scan based on the predetermined scan parameters to generate volumetric image data of the patient.

20. The system of claim 19, wherein the quality of findings is computed through: $y=A/(1+\exp(-(\text{dose}-B)/C)+D$, where y represents the quality, D represents a minimum value of a regression function, A represents a maximum excursion from D, B represents a radiation dose at which y is at a half-maximal value, and C defines a steepness of a transition between the minimum and maximum values.

* * * * *